United States Patent
Zong et al.

(10) Patent No.: US 12,048,589 B2
(45) Date of Patent: Jul. 30, 2024

(54) GUIDED ULTRASOUND IMAGING

(71) Applicant: KONINKLIJKE PHILIPS N.V., Eindhoven (NL)

(72) Inventors: Richard Zong, Bothell, WA (US); Earl M. Canfield, New Braunfels, TX (US); Gerard Joseph Harrison, Snohomish, WA (US); Anne Woodside Holmes, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 352 days.

(21) Appl. No.: 17/613,864

(22) PCT Filed: May 27, 2020

(86) PCT No.: PCT/EP2020/064714
§ 371 (c)(1),
(2) Date: Nov. 23, 2021

(87) PCT Pub. No.: WO2020/239842
PCT Pub. Date: Dec. 3, 2020

(65) Prior Publication Data
US 2022/0211348 A1  Jul. 7, 2022

Related U.S. Application Data

(60) Provisional application No. 62/855,453, filed on May 31, 2019.

(51) Int. Cl.
*A61B 8/00* (2006.01)
*A61B 8/08* (2006.01)
(Continued)

(52) U.S. Cl.
CPC .............. *A61B 8/469* (2013.01); *A61B 8/42* (2013.01); *A61B 8/483* (2013.01); *A61B 8/523* (2013.01); *G06T 7/11* (2017.01); *G06T 7/74* (2017.01)

(58) Field of Classification Search
CPC ........... A61B 8/469; A61B 8/42; A61B 8/483; A61B 8/523; A61B 2503/02; A61B 8/085;
(Continued)

(56) References Cited

U.S. PATENT DOCUMENTS 11,426,142 B2 * 8/2022 Mwikirize ........... A61B 8/0841
11,638,569 B2 * 5/2023 Mwikirize ................ G06T 7/70
382/103
(Continued)

FOREIGN PATENT DOCUMENTS

CN 105433981 A 3/2016
WO 2018205274 A1 11/2018
(Continued)

OTHER PUBLICATIONS

International Search Report and Written Opinion for PCT/EP2020/064714; Mailing date: Sep. 11, 2020, 9 pages.
(Continued)

*Primary Examiner* — Santiago Garcia

(57) ABSTRACT

The present disclosure describes imaging systems configured to generate volumetric images of a target feature based on anatomical landmarks identified during an ultrasound scan and in accordance with a user-selected view. Systems can include an ultrasound transducer configured to acquire echo signals responsive to ultrasound pulses transmitted toward a target region. A processor coupled with the transducer may present illustrative volumetric images of the target feature, each image corresponding to a particular
(Continued)

view, for a user to select. The processor can then identify anatomical landmarks corresponding to the target feature embodied within 2D image frames, and based on the identified landmarks and user-selected view, provide instructions for manipulating the transducer to a target local to generate a 2D image frame specific to the view. Echo signals are then acquired at the target locale and used to generate an actual volumetric image of the target feature corresponding to the user-selected view.

17 Claims, 8 Drawing Sheets

(51) Int. Cl.
*G06T 7/11* (2017.01)
*G06T 7/73* (2017.01)

(58) Field of Classification Search
CPC ....... A61B 8/0866; A61B 5/107; A61B 8/145; A61B 8/585; A61B 8/44; A61B 8/4444; A61B 8/4488; A61B 8/5207; A61B 8/5223; G06T 7/11; G06T 7/74; G06T 2207/10132; G06T 2207/10136; G06T 2207/20081; G06T 2207/20084; G06T 2207/30044; G06T 7/73; G16H 30/20; G16H 30/40; G16H 40/63; G16H 50/20
See application file for complete search history.

(56) References Cited

U.S. PATENT DOCUMENTS

| | | |
|---|---|---|
| 2008/0219540 A1* | 9/2008 | Ter Mors ................ G06T 15/08 |
| | | 382/132 |
| 2010/0121190 A1* | 5/2010 | Pagoulatos ............ A61B 8/483 |
| | | 600/437 |
| 2011/0255762 A1 | 10/2011 | Deischinger et al. |
| 2013/0190600 A1 | 7/2013 | Gupta et al. |
| 2016/0193482 A1* | 7/2016 | Fahrig .................... H05H 9/048 |
| | | 600/1 |
| 2017/0119354 A1* | 5/2017 | Roundhill .............. G16H 50/20 |
| 2017/0360415 A1* | 12/2017 | Rothberg ............. A61B 8/4477 |
| 2018/0132724 A1* | 5/2018 | Waechter-Stehle .......................... A61B 8/4218 |
| 2023/0036897 A1* | 2/2023 | Rouet ..................... A61B 8/42 |

FOREIGN PATENT DOCUMENTS

| | | |
|---|---|---|
| WO | 2019086365 A1 | 5/2019 |
| WO | 2019175129 A1 | 9/2019 |
| WO | 2019175141 A1 | 9/2019 |

OTHER PUBLICATIONS

Krizhevsky, Alex et al., "ImageNet Classification with Deep Convolutional Neural Networks," NIPS 2012, 9 pages.

* cited by examiner

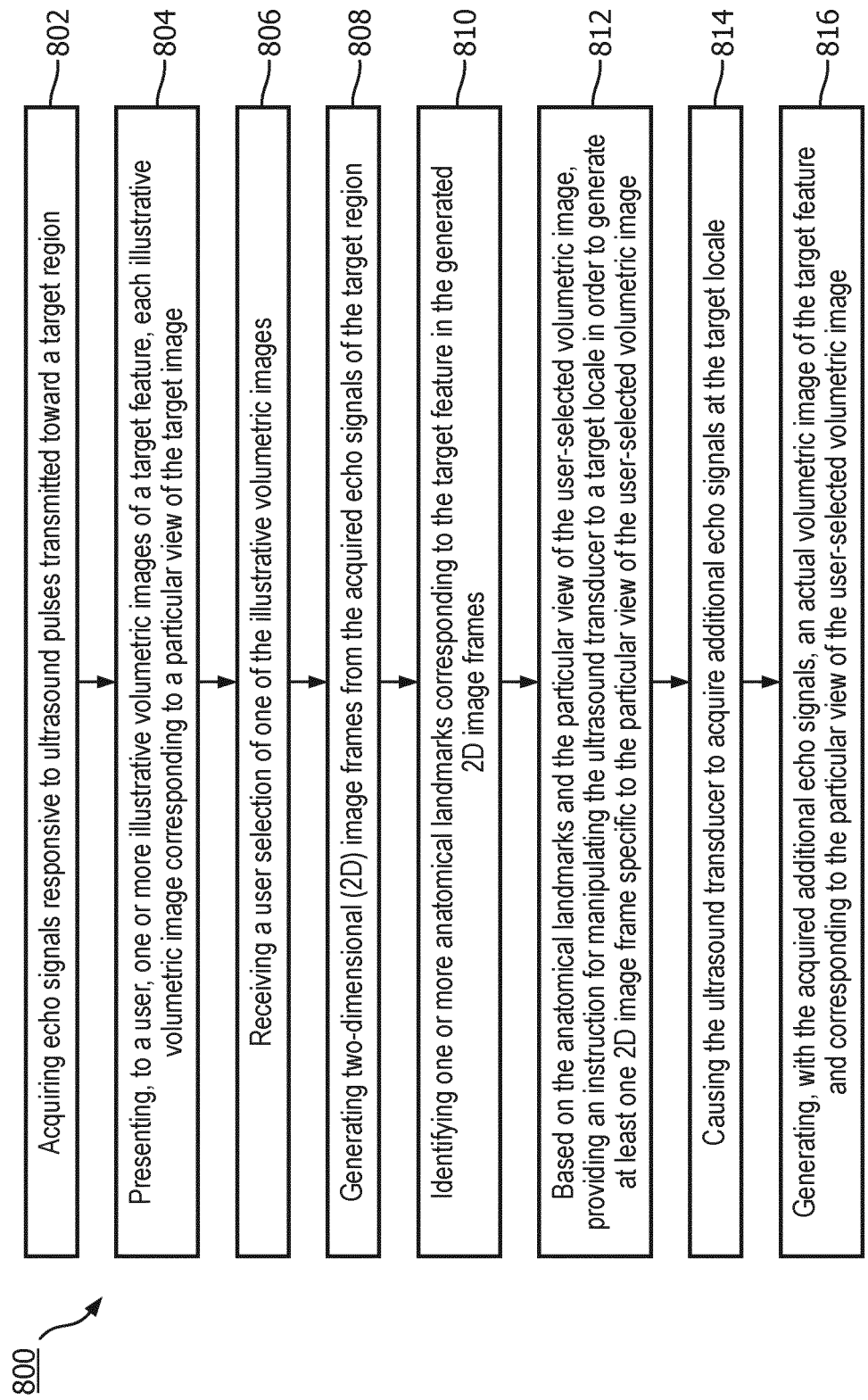

GUIDED ULTRASOUND IMAGING

CROSS-REFERENCE TO PRIOR APPLICATIONS

This application is the U.S. National Phase application under 35 U.S.C. § 371 of International Application No. PCT/EP2020/064714, filed on May 27, 2020, which claims the benefit of U.S. Provisional Patent Application No. 62/855,453, filed on May 31, 2019. These applications are hereby incorporated by reference herein.

TECHNICAL FIELD

The present disclosure pertains to ultrasound systems and methods for recognizing anatomical features via ultrasound imaging and guiding a user to capture a desired view of a target feature. Particular implementations may utilize at least one neural network and associated display configured to generate customized user instructions based on the anatomical features recognized in a current ultrasound image. Implementations also include ultrasound image acquisition components configured to automatically toggle between 2D and volumetric imaging modes.

BACKGROUND

Existing ultrasound systems can produce 3D images by acquiring and stitching together a panorama of 2D images. This particular imaging approach is especially common in prenatal applications designed to produce 3D images of a baby in the womb. Capturing detailed images of the baby face, in particular, is often desired to provide a first glimpse of the unborn baby. Unfortunately, acquiring quality images of the face can be highly dependent on the position of the baby within the womb, and ultrasound operators frequently lack the training to maneuver an ultrasound transducer in the manner necessary to overcome variation in the position of the baby. Accordingly, new technology configured to produce quality images of various anatomical features, such as the face of an unborn baby, despite the orientation of such features, is desired.

SUMMARY

The present disclosure describes systems and methods for capturing ultrasound images of various anatomical objects in accordance with a particular view selected by a user. While examples herein specifically address prenatal imaging of a fetus to acquire an image of the face of an unborn baby, it should be understood to those skilled in the art that the disclosed systems and methods are described with respect to fetal imaging for illustrative purposes only, and that anatomical imaging can be performed in accordance with the present disclosure on a variety of anatomical features, including but not limited to the heart and lungs, for instance. In some embodiments, a system may be configured to improve the accuracy, efficiency and automation of prenatal ultrasound imaging by guiding a user to acquire an image of a targeted anatomical feature, automatically selecting a region of interest (ROI) within an image of the feature, capturing a volumetric, e.g., 3D, image of the feature, and modifying the volumetric image in accordance with user preferences. The system may include an ultrasound transducer configured to acquire echo signals responsive to ultrasound pulses transmitted toward a target region, which may include the abdomen of a patient. One or more processors may be coupled with the ultrasound transducer, each processor uniquely configured to perform one or more functions based on the ultrasound data acquired by the transducer. For example, a data processor can be configured to implement one or more neural networks configured to recognize certain anatomical features and guide an operator to manipulate the transducer in the manner necessary to acquire an image of a target feature. In addition or alternatively, the data processor can be configured to perform image segmentation or another boundary detection technique to identify certain anatomical features. After defining a ROI within the image, a control circuit can be configured to automatically switch the transducer into a volumetric imaging mode for sweeping through the ROI. The acquired volumetric image may be modified, for example by a neural network or image rendering processor, configured to apply certain image modifications for improved clarity, quality and/or artistic purposes. While specific embodiments are described herein with respect to generating 3D images, the present disclosure is not limited to 3D imaging. For example, embodiments may also be directed to additional forms of volumetric imaging, such as 4D and/or spatio-temporal image correlation (STIC) imaging.

In accordance with some examples of the present disclosure, an ultrasound imaging system may include an ultrasound transducer configured to acquire echo signals responsive to ultrasound pulses transmitted toward a target region. The system may also include one or more processors in communication with the ultrasound transducer and configured to: present, to a user, one or more illustrative volumetric images of a target feature, each illustrative volumetric image corresponding to a particular view of the target image; receive a user selection of one of the illustrative volumetric images; generate two-dimensional (2D) image frames from the acquired echo signals of the target region; identify one or more anatomical landmarks corresponding to the target feature in the generated 2D image frames; based on the anatomical landmarks and the particular view of the user-selected volumetric image, provide an instruction for manipulating the ultrasound transducer to a target locale in order to generate at least one 2D image frame specific to the particular view of the user-selected volumetric image; cause the ultrasound transducer to acquire additional echo signals at the target locale; and generate, with the acquired additional echo signals, an actual volumetric image of the target feature and corresponding to the particular view of the user-selected volumetric image.

In some examples, the one or more processors are configured to identify the one or more anatomical landmarks via image segmentation. In some examples, the one or more processors are configured to identify the one or more anatomical landmarks via implementation of a neural network trained to recognize the anatomical landmarks. In some examples, the one or more processors are further configured to apply an artificial light source to the actual volumetric image in accordance with the particular view. In some examples, the artificial light source is applied by an artificial neural network. Examples can include one or more artificial neural networks, for e.g. two, three or more communicatively coupled neural networks. In some embodiments, the artificial neural networks can be further configured to apply an image contrast adjustment to the actual volumetric image in accordance with particular view. In some examples, the target feature can include the face of an unborn baby.

In some examples, the one or more processors are configured to generate the instruction for manipulating the ultrasound transducer by inputting the 2D image frames to an artificial neural network trained to compare the 2D image frames to stored image frames embodying the target feature. In some examples, the artificial neural network is configured to generate a new instruction for manipulating the ultrasound transducer upon repositioning of the ultrasound transducer. In some examples, the one or more processors are further configured to define a region of interest within the 2D image frame specific to the particular view of the user-selected volumetric image. In some examples, the ultrasound imaging system further includes a controller configured to switch the ultrasound transducer from a 2D imaging mode to a volumetric imaging mode. The controller can be configured to switch the ultrasound transducer from the 2D imaging mode to the volumetric imaging mode automatically upon receiving an indication from the one or more processors that the region of interest has been defined. Embodiments can also include a user interface communicatively coupled with the one or more processors and configured to display the instruction for manipulating the ultrasound transducer to a target locale. In some embodiments, the one or more processors can be further configured to cause an indicator of the target feature to be displayed on the user interface.

In accordance with some embodiments, a method of ultrasound imaging may involve acquiring echo signals responsive to ultrasound pulses transmitted toward a target region. The method may further involve presenting, to a user, one or more illustrative volumetric images of a target feature, each illustrative volumetric image corresponding to a particular view of the target image; receiving a user selection of one of the illustrative volumetric images; generating two-dimensional (2D) image frames from the acquired echo signals of the target region; identifying one or more anatomical landmarks corresponding to the target feature in the generated 2D image frames; based on the anatomical landmarks and the particular view of the user-selected volumetric image, providing an instruction for manipulating the ultrasound transducer to a target locale in order to generate at least one 2D image frame specific to the particular view of the user-selected volumetric image; causing the ultrasound transducer to acquire additional echo signals at the target locale; and generating, with the acquired additional echo signals, an actual volumetric image of the target feature and corresponding to the particular view of the user-selected volumetric image.

In some examples, the method further involves applying an artificial light source, an image contrast adjustment, or both to the actual volumetric image. In some examples, the target feature comprises a face of an unborn baby. In some examples, identifying the one or more anatomical landmarks involves image segmentation or implementation of at least one neural network trained to recognize the anatomical landmarks. In some examples, the method further involves displaying the instruction for manipulating the ultrasound transducer. Embodiments may also involve defining a region of interest within the 2D image frame specific to the particular view of the user-selected volumetric image. In some examples, the method also involves identifying additional anatomical landmarks of the target feature upon manipulation of an ultrasound transducer; and generating additional instructions for manipulating the ultrasound transducer based on the additional anatomical landmarks identified upon manipulation of the ultrasound transducer. Example methods may also involve switching the ultrasound transducer from the 2D imaging mode to a volumetric imaging mode upon receiving an indication that a region of interest has been identified.

Any of the methods described herein, or steps thereof, may be embodied in non-transitory computer-readable medium comprising executable instructions, which when executed may cause a processor of a medical imaging system to perform the method or steps embodied herein.

BRIEF DESCRIPTION OF THE DRAWINGS

FIG. 8 is a flow diagram of a method of ultrasound imaging performed in accordance with principles of the present disclosure.

DETAILED DESCRIPTION

Figure 1:
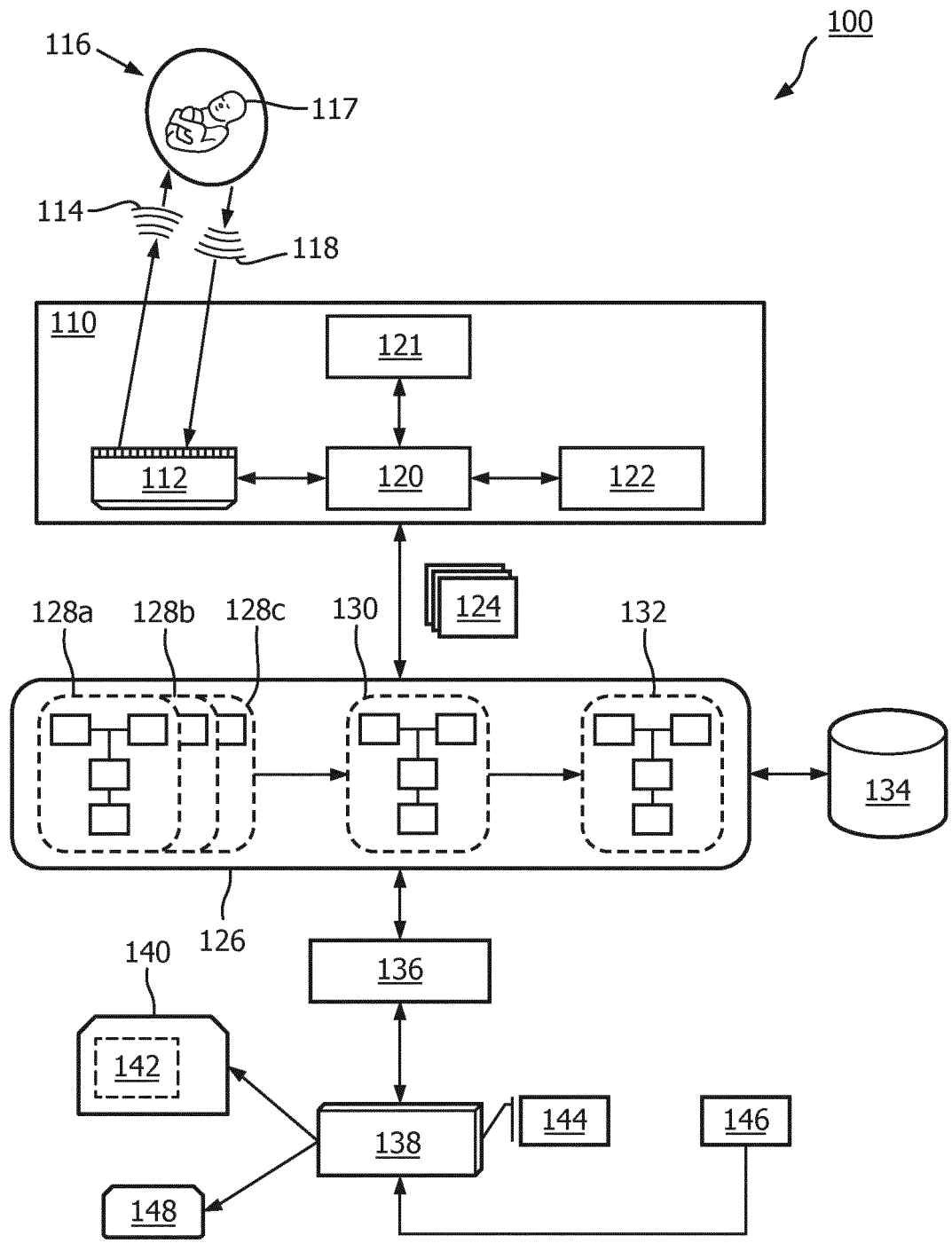
FIG. 1 is a block diagram of an ultrasound system in accordance with principles of the present disclosure.

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

An ultrasound system according to the present disclosure may utilize one or more artificial neural networks implemented by a computer processor, module or circuit. Example networks include a convolutional neural network (CNN), deep neural network (DNN), recurrent neural network (RNN), autoencoder neural network, or the like, configured to identify one or more anatomical features, e.g., head, feet, hands or legs, present within a 2D ultrasound image, and guide a user to manipulate an ultrasound transducer in the manner necessary to capture an image of a specifically targeted anatomical feature, e.g., the face of an unborn baby.

The artificial neural network(s) may be trained using any of a variety of currently known or later developed machine learning techniques to obtain a neural network (e.g., a machine-trained algorithm or hardware-based system of nodes) that is configured to analyze input data in the form of ultrasound image frames and determine the imaging adjustments necessary to acquire a particular view of at least one anatomical feature. Neural networks may provide an advantage over traditional forms of computer programming algorithms in that they can be generalized and trained to recognize data set features by analyzing data set samples rather than by reliance on specialized computer code. By presenting appropriate input and output data to a neural network training algorithm, one or more neural networks of an ultrasound system according to the present disclosure can be trained to identify a plurality of anatomical features, guide a user to obtain an image of a target feature based in part on the anatomical features identified, refine a ROI encompassing the target feature, and/or obtain a 3D image of the target feature.

An ultrasound system in accordance with principles of the present invention may include or be operatively coupled to an ultrasound transducer configured to transmit ultrasound pulses toward a medium, e.g., a human body or specific portions thereof, and generate echo signals responsive to the ultrasound pulses. The ultrasound system may include a beamformer configured to perform transmit and/or receive beamforming, and a display configured to display ultrasound images generated by the ultrasound imaging system, along with notifications overlaid on or adjacent to the images. The ultrasound imaging system may include one or more processors and at least one neural network, which may be implemented in hardware and/or software components. The neural network(s) can be machine trained to identify anatomical features present within 2D images, guide a user to obtain an image of a target feature, identify a region of interest within the image of the target feature, and/or modify a 3D image of the target feature.

The neural network(s) implemented according to some examples of the present disclosure may be hardware (e.g., neurons are represented by physical components) or software-based (e.g., neurons and pathways implemented in a software application), and can use a variety of topologies and learning algorithms for training the neural network to produce the desired output. For example, a software-based neural network may be implemented using a processor (e.g., single or multi-core CPU, a single GPU or GPU cluster, or multiple processors arranged for parallel-processing) configured to execute instructions, which may be stored in computer readable medium, and which when executed cause the processor to perform a machine-trained algorithm for evaluating an image. The ultrasound system may include a display or graphics processor, which is operable to arrange the ultrasound images and/or additional graphical information, which may include annotations, confidence metrics, user instructions, tissue information, patient information, indicators, and other graphical components, in a display window for display on a user interface of the ultrasound system. In some embodiments, the ultrasound images and associated measurements may be provided to a storage and/or memory device, such as a picture archiving and communication system (PACS) for reporting purposes or future machine training.

FIG. 1 shows an example ultrasound system according to principles of the present disclosure. The ultrasound system 100 may include an ultrasound data acquisition unit 110. The ultrasound data acquisition unit 110 can include an ultrasound probe which includes an ultrasound sensor array 112 configured to transmit ultrasound pulses 114 into a region 116 of a subject, e.g., abdomen, and receive ultrasound echoes 118 responsive to the transmitted pulses. The region 116 may include a developing fetus, as shown, or a variety of other anatomical objects, such as the heart, lungs or umbilical cord. As further shown, the ultrasound data acquisition unit 110 can include a beamformer 120, a transmit controller 121, and a signal processor 122. The transmit controller 121 can be configured to control the transmission of ultrasonic beams from the sensor array 112. An image acquisition feature that may be controlled by the transmit controller 121 is the imaging mode, e.g., 2D or 3D, implemented by the sensor array 112. For example, at the direction of the transmit controller 121, the beamformer 120 and sensor array 112 may switch from 2D imaging to 3D imaging upon acquiring a 2D image of a region of interest. The signal processor 122 can be configured to generate a stream of discrete ultrasound image frames 124 from the ultrasound echoes 118 received at the array 112.

The image frames 124 can be communicated to a data processor 126, e.g., a computational module or circuit. The data processor 126 may be configured to analyze the image frames 124 by implementing various image segmentation and/or boundary detection techniques. The data processor 126 may, in addition or alternatively, be configured to implement one or more neural networks trained to recognize various anatomical features and/or generate user instructions for manipulating the ultrasound transducer 112. In the embodiment shown, the data processor 126 can be configured to implement a first neural network 128, a second neural network 130, and/or a third neural network 132. The first neural network 128 (or networks, as further described below) may be trained to identify one or more anatomical features visible within the image frames 124, and based on the anatomical features identified, generate instructions for manipulating the ultrasound sensor array 112 in the manner necessary to obtain an image of a target feature 117, e.g., the face of an unborn baby. The second neural network 130 may be trained to identify a region of interest within the image of the target feature 117, which may trigger the sensor array 112, at the direction of the transmit controller 121, to acquire a 3D image of the region of interest. The third neural network 132 may be trained to perform one or more post-acquisition processing steps, e.g., the application of artificial lighting, necessary to generate a desired 3D portrait of the region of interest. In various examples, the data processor 126 can also be coupled, communicatively or otherwise, to a memory or database 134 configured to store various data types, including training data and newly acquired, patient-specific data.

The system 100 can also include a display processor 136, e.g., a computational module or circuit, communicatively coupled with data processor 126. The display processor 136 is further coupled with a user interface 138, such that the display processor 136 can link the data processor 126 (and thus any neural network(s) operating thereon) to the user interface 138, thereby enabling the neural network outputs, e.g., user instructions in the form of motion control commands, to be displayed on the user interface 138. In embodiments, the display processor 136 can be configured to generate 2D ultrasound images 140 from the image frames 124 received at the data processor 126, which may then be displayed via the user interface 138 in real time as an ultrasound scan is being performed. In some examples, the display processor 136 can be configured to generate and display (via user interface 138) one or more illustrative volumetric images of a target feature, each illustrative volumetric image corresponding to a particular view of the target image. The illustrative volumetric images can be selected by a user, thereby prompting the system 100 to generate and display one or more commands for acquiring and generating one or more actual volumetric images in accordance with the user-selected view. A specific region of interest ("ROI") 142, e.g., ROI box, may also be displayed. The ROI 142 may be positioned and trimmed by the second neural network 130 in some examples. One or more notifications 144, e.g., user instructions and/or alerts, may be overlaid on or displayed adjacent to the images 140 during an ultrasound scan. The user interface 138 can also be configured to receive a user input 146 at any time before, during, or after an ultrasound scan. For instance, the user interface 138 may be interactive, receiving user input 146 indicating a desired viewpoint for imaging the target feature 117 and/or indicating confirmation that an imaging instruction has been followed. The user interface 138 may also be configured to display 3D images 148 acquired and processed by the ultrasound data acquisition unit 110, data processor 126, and display processor 136. The user interface 138 may comprise a display that is positioned external to the data processor 126, for example comprising a standalone display, an augmented reality glass, or a mobile phone.

The configuration of the components shown in FIG. 1 may vary. For example, the system 100 can be portable or stationary. Various portable devices, e.g., laptops, tablets, smart phones, or the like, may be used to implement one or more functions of the system 100. In examples that incorporate such devices, the ultrasound sensor array 112 may be connectable via a USB interface, for example. In some embodiments, various components may be combined. For instance, the data processor 126 may be merged with the display processor 136 and/or the user interface 138. The first, second and/or third neural networks 128, 130, 132 may be merged such that the networks constitute sub-components of a larger, layered network, for example. In embodiments that include separate, discrete neural networks, the networks may be operatively arranged in a cascade, such that the output of the first neural network 128 comprises the input for the second neural network 130, and the output of the second neural network 130 comprises the input for the third neural network 132.

The ultrasound data acquisition unit 110 can be configured to acquire ultrasound data from one or more regions of interest 116, which may include a fetus and features thereof. The ultrasound sensor array 112 may include at least one transducer array configured to transmit and receive ultrasonic energy. The settings of the ultrasound sensor array 112 can be adjustable during a scan. For example, the ultrasound sensor array 112, under the direction of the beamformer 120 and transmit controller 121, can be configured to switch between 2D and 3D imaging modes automatically, i.e., without user input. In specific embodiments, the ultrasound sensor array 112 can be configured to switch to 3D imaging mode (or 4D or STIC mode) after the target feature 117 is identified in a 2D image 140 and the ROI 142 is demarcated. Once in 3D imaging mode, the sensor array 112 may initiate an automated sweep through the target feature 117, thereby acquiring a 3D volume of image data. A variety of transducer arrays may be used, e.g., linear arrays, convex arrays, or phased arrays. The number and arrangement of transducer elements included in the sensor array 112 may vary in different examples. For instance, the ultrasound sensor array 112 may include a 2D array of transducer elements, e.g., a matrix array probe. A 2D matrix array may be configured to scan electronically in both the elevational and azimuth dimensions (via phased array beamforming) for alternate 2D and 3D imaging. In addition to B-mode imaging, imaging modalities implemented according to the disclosures herein can also include shear-wave and/or Doppler, for example. A variety of users may handle and operate the ultrasound data acquisition unit 110 to perform the methods described herein. In some examples, the user may be an inexperienced, novice ultrasound operator.

The data acquisition unit 110 may also include a beamformer 120, e.g., comprising a microbeamformer or a combination of a microbeamformer and a main beamformer, coupled to the ultrasound sensor array 112. The beamformer 120 may control the transmission of ultrasonic energy, for example by forming ultrasonic pulses into focused beams. The beamformer 120 may also be configured to control the reception of ultrasound signals such that discernable image data may be produced and processed with the aid of other system components. The role of the beamformer 120 may vary in different ultrasound probe varieties. In some embodiments, the beamformer 120 may comprise two separate beamformers: a transmit beamformer configured to receive and process pulsed sequences of ultrasonic energy for transmission into a subject, and a separate receive beamformer configured to amplify, delay and/or sum received ultrasound echo signals. In some embodiments, the beamformer 120 may include a microbeamformer operating on groups of sensor elements for both transmit and receive beamforming, coupled to a main beamformer which operates on the group inputs and outputs for both transmit and receive beamforming, respectively.

The transmit controller 121, e.g., a computational module or circuit, may be communicatively, operatively and/or physically coupled with the sensor array 112, beamformer 120, signal processor 122, data processor 126, display processor 136, and/or user interface 138. In some examples, the transmit controller 121 may be responsive to user input 146, such that the sensor array 112, via the transmit controller 121, may switch to 3D imaging mode upon receipt of a user input directing the switch. In other examples, the transmit controller 121 may initiate the switch automatically, for example in response to an indication received from the data processor 126 that a ROI 142 has been identified in a 2D image 140 of the target feature 117.

The signal processor 122 e.g., a computational module or circuit, may be communicatively, operatively and/or physically coupled with the sensor array 112, the beamformer 120 and/or the transmit controller 121. In the example shown in FIG. 1, the signal processor 122 is included as an integral component of the data acquisition unit 110, but in other examples, the signal processor 122 may be a separate component. In some examples, the signal processor 122 may be housed together with the sensor array 112 or it may be physically separate from but communicatively (e.g., via a wired or wireless connection) coupled thereto. The signal processor 122 may be configured to receive unfiltered and disorganized ultrasound data embodying the ultrasound echoes 118 received at the sensor array 112. From this data, the signal processor 122 may continuously generate a plurality of ultrasound image frames 124 as a user scans the region 116.

In particular embodiments, the first neural network 128 may comprise a convolutional neural network trained to identify the presence and in some examples, orientation, of one or more anatomical features present in a 2D ultrasound image, e.g., a B-mode image. Based on this determination, the first neural network 128 may generate one or more user instructions for manipulating the sensor array 112 in the manner necessary to acquire an image of another anatomical feature, such as the face of an unborn baby, from a particular vantage point, which may be specified by a user. The instructions may be displayed sequentially in real time as the user adjusts the sensor array 112 in accordance with each instruction. The first neural network 128 may be configured to recognize anatomical features and generate new instructions accordingly as the user moves the sensor array 112, each new instruction based on the image data, e.g., embodying anatomical landmarks, present in each ultrasound image generated with movement of the sensor array 112. In some examples, the user may confirm that an instruction has been implemented, e.g., via manual input 146 received at the user interface 138, thereby signaling to the system that the next instruction can be displayed. Instructions can include directional commands to move, tilt or rotate the sensor array 112 in specific directions.

In some examples, the first neural network 128 can be trained to align the transducer array 112 to a target image plane based on previously acquired images stored in the database 134. The previously acquired images can be stored in association with motion control parameters and/or labels or scores for qualifying or validating newly acquired images, for example as described in PCT/EP2019/056072 and PCT/EP2019/056108, both of which are incorporated by reference in their entireties herein. Accordingly, one or more processors, e.g., data processor 126, can be configured to apply the first neural network 128 in a clinical setting to determine directional commands for the user to align the transducer array 112 to a patient in the manner necessary to acquire an image of a target feature. New motion control commands can be generated each time the transducer array 112 is repositioned. In some examples, the first neural network 128 may be further configured to predict whether a candidate of motion control configurations, e.g., controls for changing an imaging plane within a volumetric ultrasound image, used for repositioning the ultrasound transducer 112 will lead to an optimal imaging location for a particular target view given an input image. The processor may then output the directional commands in the format of instructions and/or visual indicators to the display 138 and a user may manually align the transducer array 112 to the patient based on the instructions.

In addition or alternatively, generating motion control parameters eventually displayed as instructions to a user can be achieved via implementation of multiple neural networks, or neural network layers, for example as described specifically in PCT/EP2019/056108. According to such examples, first neural network 128 may comprise networks 128a, 128b and 128c, where network 128a comprises a predictive network trained to receive a currently acquired image and infer or deduce a motion vector with the highest probability of reaching a desired location for capturing a target image view. Network 128b may comprise a fine-tuning network trained to verify whether a pair of images have the same quality level or select an image having a higher quality level from the pair. Network 128c may comprise a target network trained to determine whether a target image view has been captured.

In some embodiments, identification of the presence and orientation of one or more anatomical features present in an ultrasound image may not be performed by the first neural network. Such embodiments may involve implementation of one or more boundary detection or image segmentation techniques by one or more processors of the system 100, such as data processor 126.

The second neural network 130 may comprise a convolutional neural network trained to define a ROI 142 within a 2D image of the target feature 117. As such, the second neural network 130 may be configured to operate after the first neural network 128 has successfully guided the user to acquire an image 140 of the target feature 117. Defining the ROI 142 may involve placing and sizing a geometric shape, e.g., a box, within the image 140 of the target feature 117 such that all non-targeted features, e.g., placenta, legs, arms, neck, etc., are excluded from the ROI 142. In some examples, the ROI 142 may not comprise a geometric shape, instead comprising a best-fit line positioned around the salient features of the target feature 117, e.g., nose, forehead, eyes, chin, ears, etc. By defining the ROI 142 prior to acquisition of a 3D image, 3D data may only be collected within the ROI, which may improve the speed and efficiency of the system 100, as well as the quality of the resulting 3D image 148.

The third neural network 132 may comprise a convolutional neural network trained to perform one or more post-acquisition processing steps necessary to generate a 3D panoramic image 148 of the ROI 142. Example post-acquisition processing steps may include applying an artificial light source to the image, such that the image includes shadows. The direction from which the artificial light source is applied may be adjusted automatically by the third neural network 132 or in response to user input 146. The third neural network 132 may also trim the image to remove one or more undesired features. In addition or alternatively, the third neural network 132 may be configured to alter the imaging contrast, such that certain features are accentuated or dimmed. The modifications introduced by the third neural network 132 may be based, at least in part, on artistic qualities. For example, the lighting, contrast and/or trimming adjustments applied by the third neural network 132 may be designed to improve the aesthetic appearance of the 3D portrait generated by the system.

In some embodiments, one or more of the post-acquisition steps, such as application of an artificial light source, may be implemented without a neural network. For example, one or more processors of the system 100, such as data processor 126 or display processor 136, may be configured to render the 3D image 148 of the ROI 142 in spatial relation to a lighting model such that lighting and shadowing regions of the anatomical features depicted within the ROI 142 are displayed according to a stored setting of the system 100, as disclosed for instance in US 2017/0119354, which is incorporated by reference in its entirety herein. The stored setting used for the lighting model can be automatically implemented by the system 100, or the stored setting can be customizable or selectable from a plurality of setting options.

Each neural network 128, 130 and 132 may be implemented, at least in part, in a computer-readable medium comprising executable instructions, which when executed by a processor, e.g., data processor 126, may cause the processor to perform a machine-trained algorithm. For example, the data processor 126 may be caused to perform a machine-trained algorithm to determine the presence and/or type of anatomical features contained in an image frame based on the acquired echo signals embodied therein. The data processor 126 may also be caused to perform a separate machine-trained algorithm to define the location, size and/or shape of a ROI within an image frame, such as a 2D image frame containing an image of the face of an unborn baby. Another machine-trained algorithm implemented by the data processor 126 may apply at least one image display setting configured to add shading and/or contrast to a 3D image.

To train each neural network 128, 130 and 132, training sets which include multiple instances of input arrays and output classifications may be presented to the training algorithm(s) of each network (e.g., AlexNet training algorithm, as described by Krizhevsky, A., Sutskever, I. and Hinton, G. E. "*ImageNet Classification with Deep Convolutional Neural Networks,*" NIPS 2012 or its descendants). The first neural network 128 can be trained using a large clinical database of ultrasound images obtained during prenatal ultrasound scans. The images may include fetuses at various stages of development from various imaging angles and positions. A neural network training algorithm associated with the first neural network 128 can be presented with thousands or even millions of training data sets in order to train the neural network to identify anatomical features and determine the ultrasound probe adjustments necessary to acquire an image of a target feature based on the presence of the features identified. In various examples, the number of ultrasound images used to train the first neural network 128 may range from about 50,000 to 200,000 or more. The number of images used to train the first neural network 128 may be increased if higher numbers of different anatomical features are to be recognized. The number of training images may differ for different anatomical features, and may depend on variability in the appearance of certain features. For example, certain features may appear more consistently at certain stages of prenatal development than other features. Training the first neural network 128 to identify features with moderate to high variability may require more training images. The first neural network 128 may be further trained with clinically validated instructions for manipulating an ultrasound probe, each instruction associated with an initial set of anatomical features present in a current ultrasound image and a target anatomical feature viewed from a particular vantage point. Accordingly, the first neural network 128 may be trained to recognize certain anatomical features present within a given ultrasound image and associate such features with one or more instructions necessary to acquire an image of a target feature from a vantage point.

The second neural network 130 can also be trained using a large clinical database of ultrasound images obtained during prenatal ultrasound scans. Each of the training images may contain a defined ROI, which may include the boundaries of the face of an unborn baby. A neural network training algorithm associated with the second neural network 130 can be presented with thousands or even millions of training data sets in order to train the neural network to define a ROI within any given 2D ultrasound image. In various examples, the number of ultrasound images used to train the second neural network 130 may range from about 50,000 to 200,000 or more. The number of training images may be increased for greater numbers of viewing options. For example, if the target feature can only be imaged from one direction, the number of training images may be less compared to embodiments in which the target feature can be imaged from multiple directions.

The third neural network 132 can also be trained using a large clinical database of ultrasound images obtained during prenatal ultrasound scans. Each of the images may contain a 3D image of a target feature with one or more post-acquisition settings applied. For example, each image may include an artificial light source, pixel contrast adjustments, and/or feature trimming modifications, just to name a few, so that the third neural network 132 can learn which adjustments to apply to different images to ensure that a recognizable image of the target feature, e.g., baby face, is generated in accordance with common artistic preferences. The number of ultrasound images used to train the third neural network 132 may range from about 50,000 to 200,000 or more. The number of training images may be increased to accommodate a greater number of post-acquisition modifications.

Figure 2:
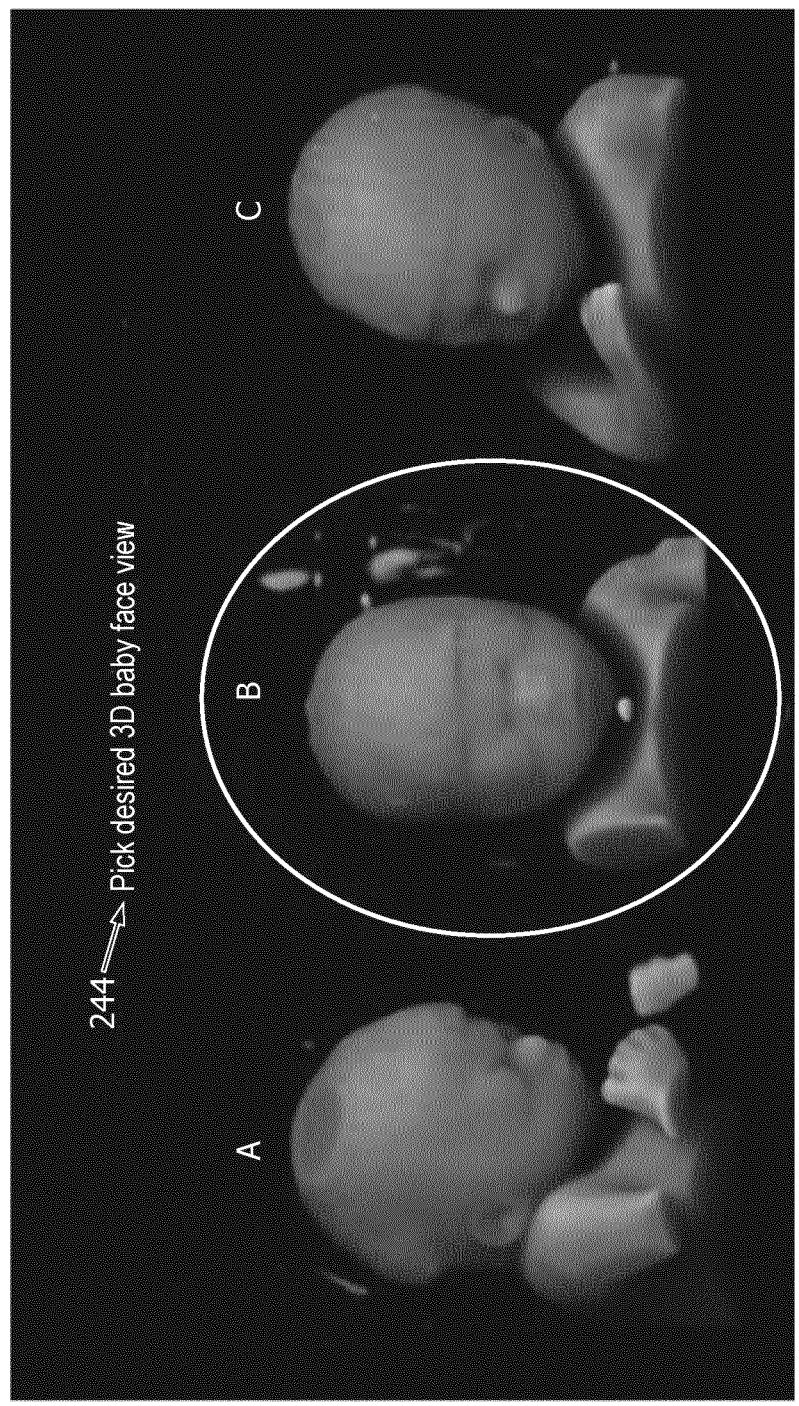
FIG. 2 is a display of target feature viewing options presented on a user interface in accordance with principles of the present disclosure.

FIG. 2 is a display of illustrative volumetric images of a target feature generated by one or more processors described herein. The illustrative volumetric images are presented as selectable options to a user on a user interface 238, along with a user instruction 244 to "Pick Desired 3D Baby Face View." In the example shown, the target feature includes the face of an unborn baby. A user may select option A, B or C corresponding to a right profile view, center front view, and left profile view of the baby face, respectively. Selection of option B, as shown, may trigger one or more processors operating on the system, which may be configured to implement one or more neural networks, coupled with the user interface 238 to generate user instructions for manipulating an ultrasound transducer to a target locale in order to acquire and generate at least one image frame in accordance with the specific view embodied by option B.

Figure 3:
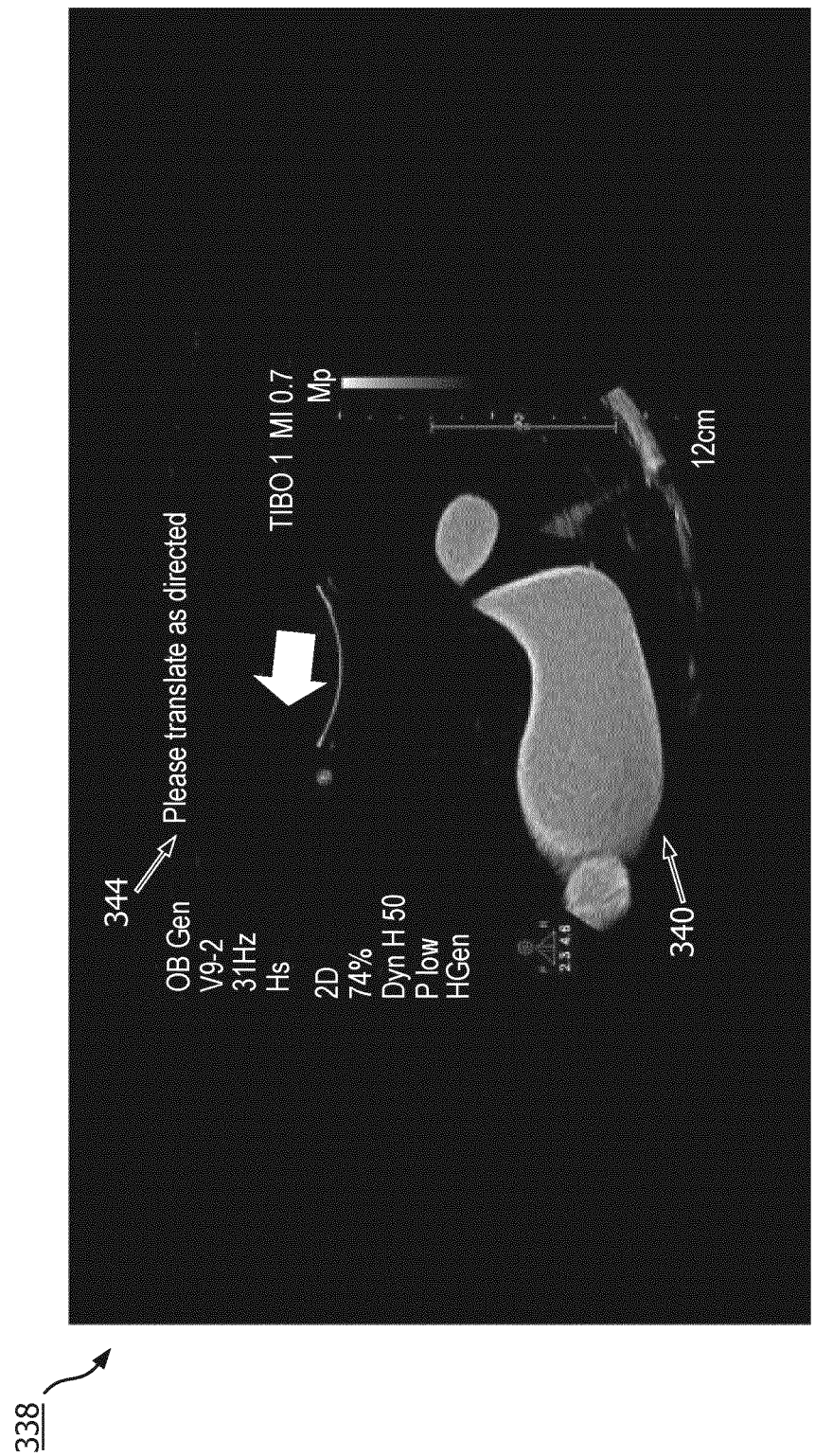
FIG. 3 is a display of a user instruction for ultrasound probe manipulation overlaid on a live 2D image generated in accordance with principles of the present disclosure.

FIG. 3 is a display of a user instruction 344 for ultrasound probe manipulation overlaid on a live 2D image 340 of a fetus displayed on a user interface 338. User instructions for ultrasound probe manipulation, such as user instruction 344, may be generated by data processor 126, implementing one or more neural networks and/or image segmentation techniques, and output to the user interface 138 for display.

With respect to the ultrasound probe used to acquire the image 340, the user instruction 344 directs the user to "Please Translate As Directed." The exact language of the user instruction 344 may vary. In some examples, the instruction may consist of one or more symbols, e.g., an arrow, only. In still other examples, the instruction may not be visually displayed at all, and may instead by conveyed as an audio cue. The user instruction 344 is generated based on fetal anatomical landmarks recognized by a neural network operating within the ultrasound system, and also based on the viewing option selected by the user, as shown in FIG. 2.

In additional implementations, visual indicators embodying user instructions may include a graphical representation or view of the ultrasound probe, including one or more features of the probe, such as the handle, one or more adjustable knobs, and/or a switch. According to such examples, user instructions may include indicating a direction and/or an amount to dial the knobs, an instruction to turn the switch on or off, and/or a direction and/or a degree to rotate the probe. In some examples, motion control commands can include controls for operating the probe (or other imaging device) to change an imaging plane within a volumetric ultrasound image in addition to changing a physical location of the probe. In general, user instructions can include motion control commands embodying any measurable data related to a particular position or motion of an imaging device, e.g., ultrasound transducer, as further described in PCT/EP2019/056072 and PCT/EP2019/056108.

Figure 4:
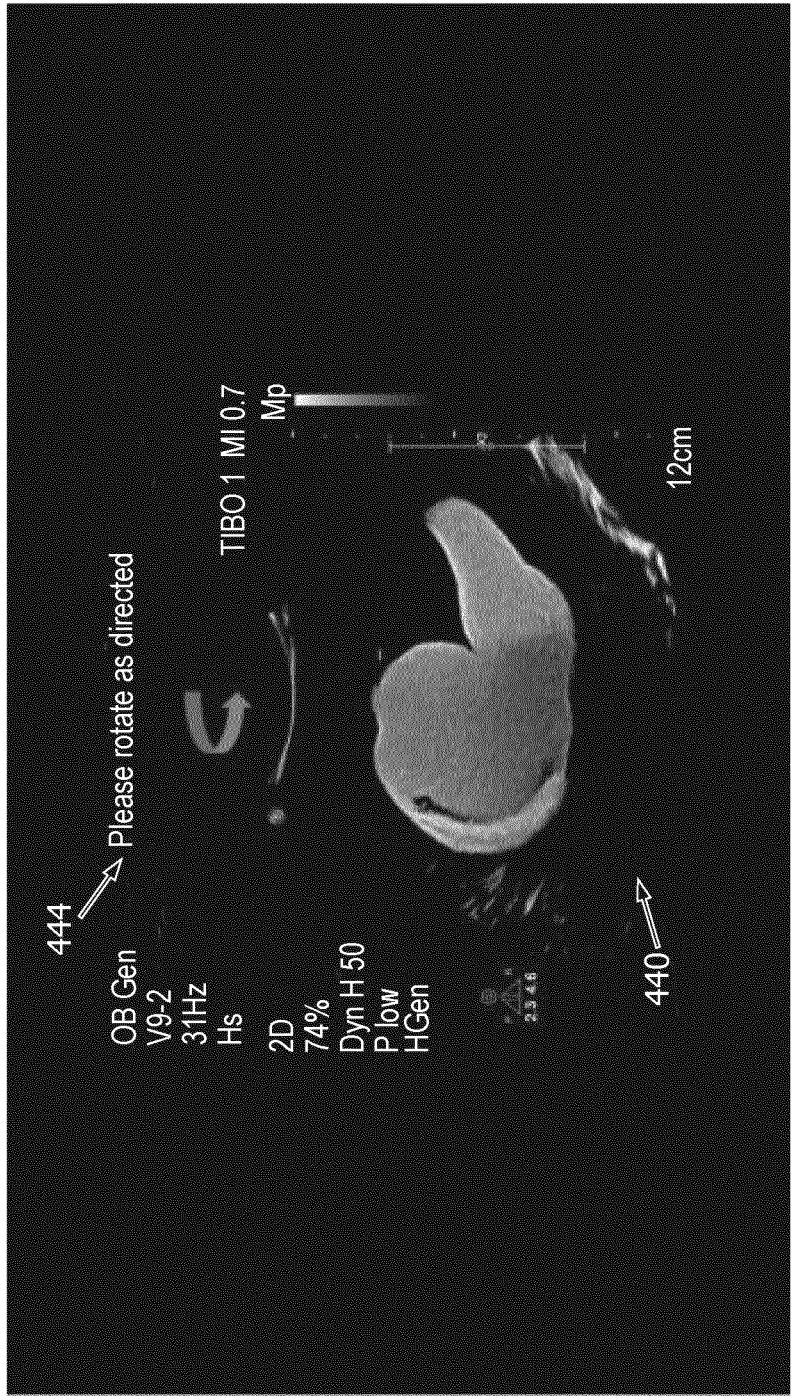
FIG. 4 is a display of another user instruction for ultrasound probe manipulation overlaid on a live 2D image generated in accordance with principles of the present disclosure.

FIG. 4 is a display of another user instruction 444 for ultrasound probe manipulation overlaid on a live 2D image 440 of a fetus displayed on a user interface 438. At this stage, the user instruction 444 directs the user to "Please Rotate As Directed." The user instruction 444 may be generated based on the fetal anatomical landmarks recognized in the image 440 by one or more processors, and also based on the viewing option selected by the user, as shown in FIG. 2.

Figure 5:
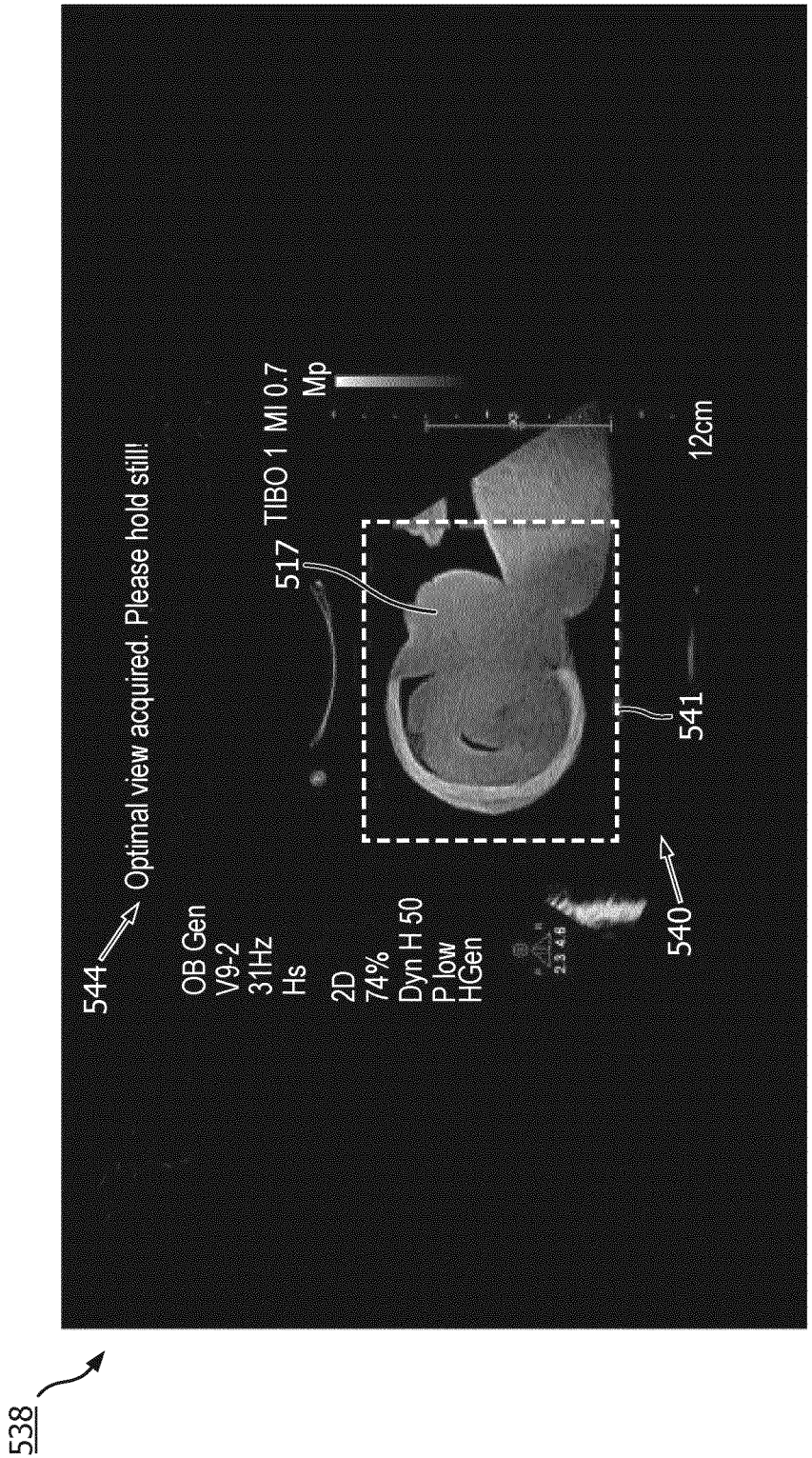
FIG. 5 is a display of another user instruction for ultrasound probe manipulation overlaid on a live 2D image generated in accordance with principles of the present disclosure.

FIG. 5 is a display of another user instruction 544 for ultrasound probe manipulation overlaid on a live 2D image 540 of a fetus displayed on a user interface 538. At this stage, the target feature 517, i.e., the baby face, is in view, along with a preliminary ROI 541. The user instruction 544 informs the user that "Optimal View Acquired" and thus directs the user to "Please Hold Still!" The user instruction 544 may be generated based on facial landmarks recognized in the image 540 by the neural network or other processing component, and also based on the viewing option selected by the user, as shown in FIG. 2.

Figure 6:
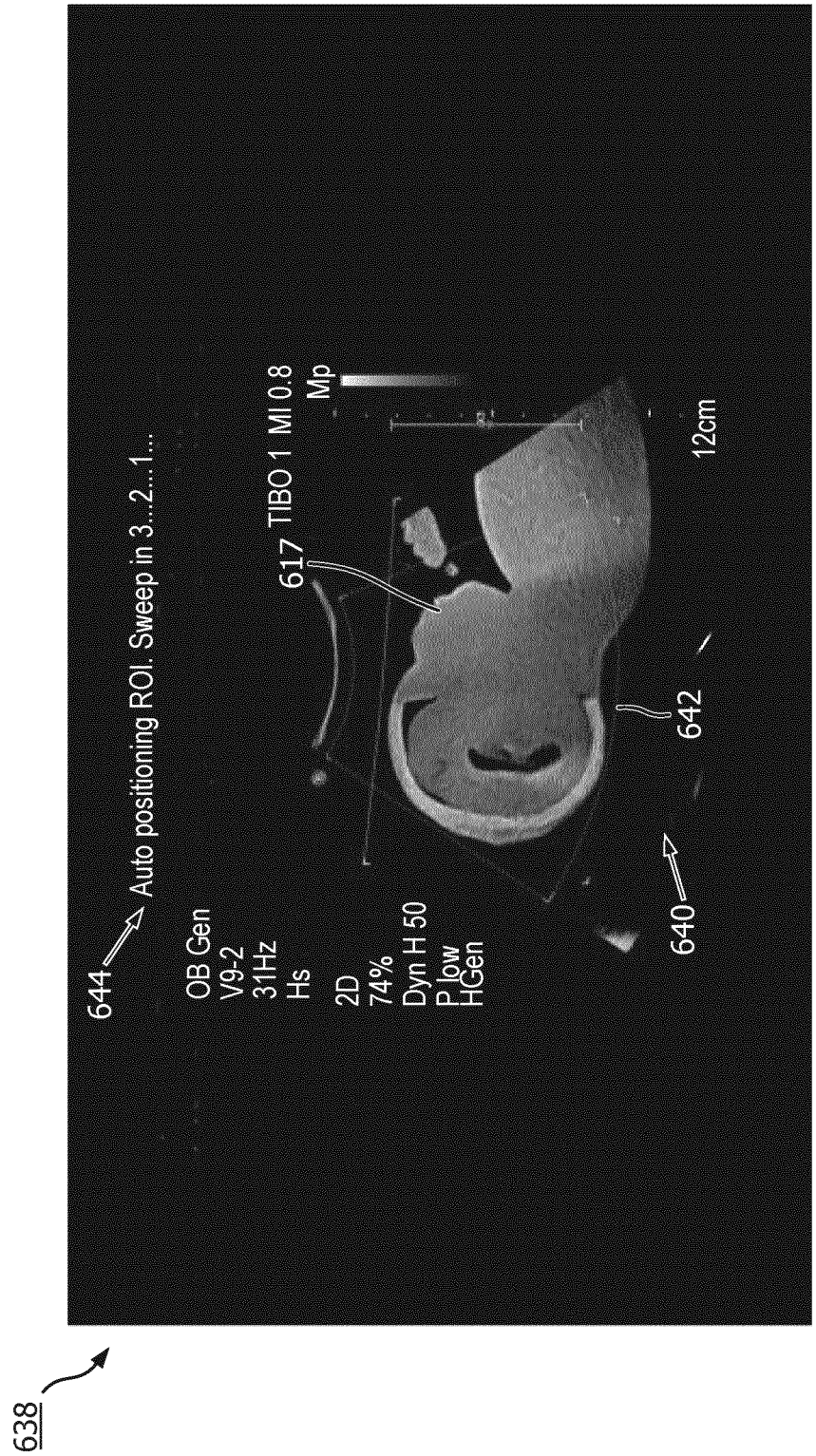
FIG. 6 is a display showing automatic positioning of a region of interest on a live 2D image in accordance with principles of the present disclosure.

FIG. 6 is a display showing automatic positioning of a refined ROI 642 along with a user notification 644 indicating the impending commencement of a 3D sweep. A separate neural network, in embodiments featuring multiple discrete networks, can be configured to identify and define the refined ROI 642 by distinguishing facial features from non-facial features, and trimming the preliminary ROI 541 (of FIG. 5) to include the facial features, only. In addition or alternatively, facial features may be identified and trimmed via image segmentation. After the refined ROI 642 is defined, the system may perform a 3D sweep of the target feature 617 within the refined ROI 642. The user interface 638 may prompt the user to confirm whether the sweep should proceed, or may alert the user that the sweep will be performed automatically, for example at the end of a countdown. Accordingly, the user notification 644 may inform the user that "Auto Positioning ROI. Sweep in 3 . . . 2 . . . 1 . . . ."

Figure 7:
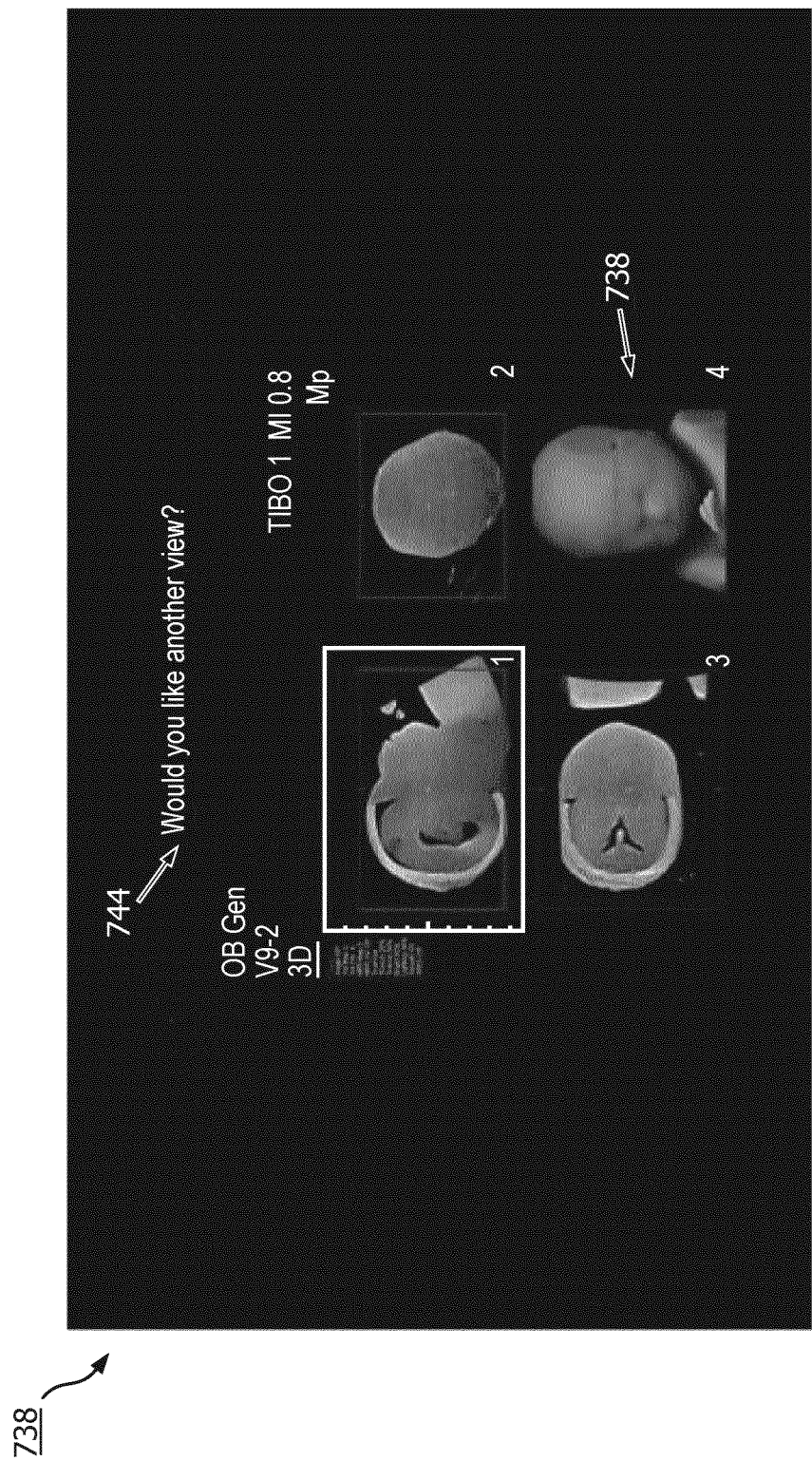
FIG. 7 is a display of additional target feature viewing options presented on a user interface in accordance with principles of the present disclosure.

FIG. 7 is a display of an actual volumetric image of the target feature captured in the refined ROI 642 (of FIG. 6). In the example shown, the actual image comprises an acquired 3D image 748 of the refined ROI 642 presented on a user interface 738, along with a user notification 744 asking "Would you like another view?" As shown, the 3D image 748 includes shadows generated by an artificial light source, which may be applied by another processor and/or neural network operating on the system. If the user indicates that another view is desired, the user interface may display the initial viewing options, for example in the same or similar manner shown in FIG. 2.

Certain 3D images may be unobtainable, for example due to the position of a fetus. In such cases, an underlying neural network, such as the first neural network 128 depicted in FIG. 1, may be configured to recognize which views will yield a quality image of the target feature. Such view(s) may be displayed on a user interface for selection by the user, thereby initiating the display of user instructions necessary to acquire the image, as shown in FIGS. 2-7.

FIG. 8 is a flow diagram of a method of ultrasound imaging performed in accordance with principles of the present disclosure. The example method 800 shows the steps that may be utilized, in any sequence, by the systems and/or apparatuses described herein for acquiring a 3D image of a target feature, such as the face of an unborn baby, which may be performed by a novice user adhering to instructions generated by the system. The method 800 may be performed by an ultrasound imaging system, such as system 100, or other systems including, for example, a mobile system such as LUMIFY by Koninklijke Philips N.V. ("Philips"). Additional example systems may include SPARQ and/or EPIQ, also produced by Philips.

In the embodiment shown, the method 800 begins at block 802 by "acquiring echo signals responsive to ultrasound pulses transmitted toward a target region."

At block 804, the method involves "presenting, to a user, one or more illustrative volumetric images of a target feature, each illustrative volumetric image corresponding to a particular view of the target image."

At block 806, the method involves "receiving a user selection of one of the illustrative volumetric images."

At block 808, the method involves "generating two-dimensional (2D) image frames from the acquired echo signals of the target region."

At block 810, the method involves "identifying one or more anatomical landmarks corresponding to the target feature in the generated 2D image frames."

At block 812, the method involves "based on the anatomical landmarks and the particular view of the user-selected volumetric image, providing an instruction for manipulating the ultrasound transducer to a target locale in order to generate at least one 2D image frame specific to the particular view of the user-selected volumetric image."

At block 814, the method involves "causing the ultrasound transducer to acquire additional echo signals at the target locale."

At block 816, the method involves "generating, with the acquired additional echo signals, an actual volumetric image of the target feature and corresponding to the particular view of the user-selected volumetric image."

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
   an ultrasound transducer configured to acquire echo signals responsive to ultrasound pulses transmitted toward a target region;
   one or more processors in communication with the ultrasound transducer and configured to:
     present, to a user, one or more illustrative volumetric images of a target feature, each illustrative volumetric image corresponding to a particular view of the target image;
     receive a user selection of one of the illustrative volumetric images;
     generate two-dimensional (2D) image frames from the acquired echo signals of the target region;
     identify one or more anatomical landmarks corresponding to the target feature in the generated 2D image frames;
     based on the anatomical landmarks and the particular view of the user-selected volumetric image, provide an instruction for manipulating the ultrasound transducer to a target locale in order to generate at least one 2D image frame specific to the particular view of the user-selected volumetric image;
     cause the ultrasound transducer to acquire additional echo signals at the target locale; and a controller configured to switch the ultrasound transducer from a 2D imaging mode to a volumetric imaging mode, wherein the controller is configured to switch the ultrasound transducer from the 2D imaging mode to the volumetric imaging mode automatically upon receiving an indication from the one or more processors that a region of interest has been defined within the 2D image frame specific to the particular view of the user-selected volumetric image,
     wherein the one or more processors are further configured to generate, with the acquired additional echo signals, an actual volumetric image of the target feature and corresponding to the particular view of the user-selected volumetric image.

2. The ultrasound imaging system of claim 1, wherein the one or more processors are configured to identify the one or more anatomical landmarks via image segmentation.

3. The ultrasound imaging system of claim 1, wherein the one or more processors are configured to identify the one or more anatomical landmarks via implementation of a neural network trained to recognize the anatomical landmarks.

4. The ultrasound imaging system of claim 1, wherein the one or more processors are further configured to apply an artificial light source to the actual volumetric image in accordance with the particular view.

5. The ultrasound imaging system of claim 1, wherein the target feature comprises a face of an unborn baby.

6. The ultrasound imaging system of claim 1, wherein the one or more processors are configured to generate the instruction for manipulating the ultrasound transducer by inputting the 2D image frames to an artificial neural network trained to compare the 2D image frames to stored image frames embodying the target feature.

7. The ultrasound imaging system of claim 6, wherein the artificial neural network is configured to generate a new instruction for manipulating the ultrasound transducer upon repositioning of the ultrasound transducer.

8. The ultrasound imaging system of claim 1, further comprising a user interface communicatively coupled with the one or more processors and configured to display the instruction for manipulating the ultrasound transducer to the target locale.

9. A method of ultrasound imaging, the method comprising:
   acquiring echo signals responsive to ultrasound pulses transmitted toward a target region;
   presenting, to a user, one or more illustrative volumetric images of a target feature, each illustrative volumetric image corresponding to a particular view of the target image;
   receiving a user selection of one of the illustrative volumetric images;
   generating two-dimensional (2D) image frames from the acquired echo signals of the target region;
   identifying one or more anatomical landmarks corresponding to the target feature in the generated 2D image frames;
   based on the anatomical landmarks and the particular view of the user-selected volumetric image, providing an instruction for manipulating the ultrasound transducer to a target locale in order to generate at least one 2D image frame specific to the particular view of the user-selected volumetric image;
   causing the ultrasound transducer to acquire additional echo signals at the target locale;

automatically switching the ultrasound transducer from a 2D imaging mode to a volumetric imaging mode upon receiving an indication that the target feature has been identified; and generating, with the acquired additional echo signals, an actual volumetric image of the target feature and corresponding to the particular view of the user-selected volumetric image.

10. The method of claim 9, further comprising applying an artificial light source, an image contrast adjustment, or both to the actual volumetric image.

11. The method of claim 9, wherein the target feature comprises a face of an unborn baby.

12. The method of claim 9, wherein identifying the one or more anatomical landmarks involves image segmentation or implementation of at least one neural network trained to recognize the anatomical landmarks.

13. The method of claim 9, further comprising displaying the instruction for manipulating the ultrasound transducer.

14. The method of claim 9, further comprising defining a region of interest within the 2D image frame specific to the particular view of the user-selected volumetric image.

15. The method of claim 9, further comprising:
identifying additional anatomical landmarks of the target feature upon manipulation of an ultrasound transducer; and generating additional instructions for manipulating the ultrasound transducer based on the additional anatomical landmarks identified upon manipulation of the ultrasound transducer.

16. The method of claim 9, further comprising switching the ultrasound transducer from the 2D imaging mode to a volumetric imaging mode upon receiving an indication that a region of interest has been identified.

17. A non-transitory computer-readable medium comprising executable instructions, which when executed cause a processor of a medical imaging system to perform any of the method of claim 9.

* * * * *